(12) United States Patent
Attawia et al.

(10) Patent No.: US 8,728,523 B2
(45) Date of Patent: *May 20, 2014

(54) TRANSDISCAL ADMINISTRATION OF SPECIFIC INHIBITORS OF PRO-INFLAMMATORY CYTOKINES

(75) Inventors: Mohamed Attawia, Holmdel, NJ (US); Thomas M. DiMauro, Southboro, MA (US); Hassan Serhan, South Easton, MA (US); Sudhakar Kadiyala, Newton, MA (US); David Urbahns, Barrington, RI (US); Scott Bruder, Franklin Lakes, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 844 days.

This patent is subject to a terminal disclaimer.

(21) Appl. No.: 12/291,378

(22) Filed: Nov. 7, 2008

(65) Prior Publication Data

US 2009/0175943 A1 Jul. 9, 2009

Related U.S. Application Data

(60) Continuation of application No. 11/881,926, filed on Jul. 30, 2007, which is a division of application No. 10/456,948, filed on Jun. 6, 2003, now Pat. No. 7,344,716.

(60) Provisional application No. 60/470,098, filed on May 13, 2003.

(51) Int. Cl.
*A61K 45/00* (2006.01)
*A61K 39/395* (2006.01)

(52) U.S. Cl.
USPC ............ 424/484; 424/133.1; 424/145.1; 424/85.1; 424/130.1; 424/141.1

(58) Field of Classification Search
None
See application file for complete search history.

(56) References Cited

U.S. PATENT DOCUMENTS

| | | | |
|---|---|---|---|
| 3,678,158 A | 7/1972 | Sussman | |
| 4,341,867 A | 7/1982 | Johansen | |
| 4,427,649 A | 1/1984 | Dingle et al. | |
| 4,435,506 A | 3/1984 | Jackson et al. | |
| 4,696,816 A | 9/1987 | Brown | |
| 5,095,037 A | 3/1992 | Iwamitsu et al. | |
| 5,116,964 A | 5/1992 | Capon et al. | |
| 5,194,596 A | 3/1993 | Tischer et al. | |
| 5,223,248 A | 6/1993 | McNamara et al. | |
| 5,225,538 A | 7/1993 | Capon et al. | |
| 5,231,024 A | 7/1993 | Moeller et al. | |
| 5,258,371 A | 11/1993 | Golub et al. | |
| 5,270,300 A | 12/1993 | Hunziker | |
| 5,368,841 A | 11/1994 | Trauner et al. | |
| 5,447,851 A | 9/1995 | Beutler et al. | |
| 5,510,370 A | 4/1996 | Hock | |
| 5,602,156 A | 2/1997 | Kohn et al. | |
| 5,656,272 A | 8/1997 | Le et al. | |
| 5,656,644 A | 8/1997 | Adams et al. | |
| 5,728,396 A | 3/1998 | Peery et al. | |
| 5,827,886 A | 10/1998 | Hersh | |
| 5,833,984 A | 11/1998 | Eibl et al. | |
| 5,842,477 A | 12/1998 | Naughton et al. | |
| 5,942,499 A | 8/1999 | Radomsky | |
| 5,965,583 A | 10/1999 | Beers et al. | |
| 6,015,557 A * | 1/2000 | Tobinick et al. ......... | 424/134.1 |
| 6,049,026 A | 4/2000 | Muschler | |
| 6,277,969 B1 | 8/2001 | Le et al. | |
| 6,284,471 B1 | 9/2001 | Le et al. | |
| 6,288,062 B1 | 9/2001 | Adams et al. | |
| 6,294,170 B1 | 9/2001 | Boone et al. | |
| 6,300,347 B1 | 10/2001 | Revesz | |
| 6,340,369 B1 * | 1/2002 | Ferree ...................... | 623/17.11 |
| 6,352,557 B1 | 3/2002 | Ferree | |
| 6,419,944 B2 | 7/2002 | Tobinick | |
| 6,541,477 B2 | 4/2003 | Goehring et al. | |
| 6,554,830 B1 | 4/2003 | Chappius | |
| 6,590,081 B1 | 7/2003 | Zhang | |
| 6,593,310 B1 | 7/2003 | Cullis-Hill | |
| 6,623,472 B1 | 9/2003 | Reincke et al. | |
| 6,713,246 B1 | 3/2004 | Reinecke et al. | |
| 6,756,215 B1 | 6/2004 | Wolfraim et al. | |
| 7,067,144 B2 | 6/2006 | Demopulos et al. | |
| 7,097,834 B1 | 8/2006 | Boyle | |
| 7,344,716 B2 * | 3/2008 | DiMauro et al. ......... | 424/145.1 |
| 7,429,378 B2 | 9/2008 | Serhan et al. | |
| 7,553,827 B2 | 6/2009 | Attawia et al. | |
| 7,727,954 B2 | 6/2010 | McKay | |
| 7,741,273 B2 | 6/2010 | McKay | |
| 7,799,782 B2 | 9/2010 | Munson et al. | |

(Continued)

FOREIGN PATENT DOCUMENTS

AU 2003/263340 A1 3/2004
EP 0 218 868 A2 4/1987

(Continued)

OTHER PUBLICATIONS

El-Khoury (Am J Roentgenol. 1991;157(4):685-691).*
Abbas-Ghaleb, K., et al., "Preconcentration of Selenium Compounds on a Porous Graphitic Carbon Column in View of HPLC-ICP-AES Speciation Analysis," *Anal. Bioanal. Chem.*, 377: 1026-1031 (2003).
Ahn, N., et al., "Effect of Nutrient Concentration and OP-1 on the Metabolism of Intervertebral Disc: In Vitro Organ Culture Study," 28, *Abstracts of the 30th Annual Meeting of the International Society for the Study of the Lumbar Spine*, Vancouver, Canada (May 2003).
Alini, M., et al., "A Biological Approach in Treating Disc Degeneration: Not for Today, but Maybe for Tomorrow," *Eur. Spine J.*, 11(Supp.2): S215-S220 (2002).

(Continued)

*Primary Examiner* — Cherie M Stanfield
(74) *Attorney, Agent, or Firm* — Hamilton, Brook, Smith & Reynolds, P.C.

(57) ABSTRACT

The present invention relates to injecting a high specificity cytokine antagonist into a diseased intervertebral disc.

19 Claims, No Drawings

(56) References Cited

U.S. PATENT DOCUMENTS

| | | | |
|---|---|---|---|
| 8,067,397 B2 | 11/2011 | Attawia et al. | |
| 8,273,347 B2 | 9/2012 | Attawia et al. | |
| 8,333,960 B2 | 12/2012 | Attawia et al. | |
| 8,361,467 B2 | 1/2013 | DiMauro et al. | |
| 2001/0006948 A1 | 7/2001 | Kang et al. | |
| 2001/0016195 A1 | 8/2001 | Tobinick | |
| 2001/0026801 A1 | 10/2001 | Tobinick | |
| 2002/0010471 A1 | 1/2002 | Wironen et al. | |
| 2002/0019351 A1 | 2/2002 | Ke et al. | |
| 2002/0026244 A1* | 2/2002 | Trieu | 623/17.16 |
| 2002/0032155 A1 | 3/2002 | Ferree | |
| 2002/0082697 A1 | 6/2002 | Damien | |
| 2002/0107200 A1 | 8/2002 | Chang et al. | |
| 2002/0169162 A1 | 11/2002 | Smith et al. | |
| 2002/0198599 A1 | 12/2002 | Haldimann | |
| 2003/0007972 A1 | 1/2003 | Tobinick | |
| 2003/0008817 A1 | 1/2003 | Sander et al. | |
| 2003/0039651 A1 | 2/2003 | Olmarker | |
| 2003/0049256 A1 | 3/2003 | Tobinick | |
| 2003/0069639 A1 | 4/2003 | Sander et al. | |
| 2003/0134792 A1 | 7/2003 | Pike et al. | |
| 2003/0207827 A1 | 11/2003 | Boyle et al. | |
| 2003/0220692 A1 | 11/2003 | Shapiro et al. | |
| 2003/0235585 A1 | 12/2003 | Fischkoff et al. | |
| 2003/0235589 A1 | 12/2003 | Demopulos et al. | |
| 2004/0022864 A1 | 2/2004 | Freyman et al. | |
| 2004/0126372 A1 | 7/2004 | Banerjee et al. | |
| 2004/0193274 A1 | 9/2004 | Trieu | |
| 2004/0228853 A1 | 11/2004 | Serhan et al. | |
| 2004/0229786 A1 | 11/2004 | Attawia et al. | |
| 2004/0229878 A1 | 11/2004 | DiMauro et al. | |
| 2005/0025765 A1 | 2/2005 | DiMauro et al. | |
| 2005/0038001 A1 | 2/2005 | Attawia et al. | |
| 2005/0054595 A1 | 3/2005 | Binette et al. | |
| 2005/0080113 A1 | 4/2005 | Ohkawa et al. | |
| 2005/0090501 A1 | 4/2005 | Collis et al. | |
| 2005/0100538 A1 | 5/2005 | Mohamed et al. | |
| 2005/0112091 A1 | 5/2005 | DiMauro et al. | |
| 2005/0282783 A1 | 12/2005 | Bujoli et al. | |
| 2006/0193920 A1 | 8/2006 | Bosch et al. | |
| 2006/0210552 A1 | 9/2006 | Demopulos et al. | |
| 2007/0237777 A1 | 10/2007 | DiMauro et al. | |
| 2007/0243228 A1 | 10/2007 | McKay | |
| 2007/0269413 A1 | 11/2007 | Serhan et al. | |
| 2008/0213261 A1 | 9/2008 | DiMauro et al. | |
| 2009/0068270 A1 | 3/2009 | Attawia et al. | |
| 2009/0155364 A1 | 6/2009 | Serhan et al. | |
| 2009/0162351 A1 | 6/2009 | Brown et al. | |
| 2009/0162376 A1 | 6/2009 | Brown et al. | |
| 2009/0324558 A1 | 12/2009 | Attawia et al. | |
| 2010/0158800 A1 | 6/2010 | McKay | |
| 2010/0189757 A1 | 7/2010 | McKay | |

FOREIGN PATENT DOCUMENTS

| | | |
|---|---|---|
| EP | 0 288 088 B1 | 10/1988 |
| EP | 0 438 234 A1 | 7/1991 |
| EP | 0 950 417 A2 | 10/1999 |
| EP | 1 133 995 A2 | 9/2001 |
| EP | 1 153 607 A2 | 11/2001 |
| EP | 1 464 307 A1 | 10/2004 |
| WO | WO 91/02078 A1 | 2/1991 |
| WO | WO 92/07076 A1 | 4/1992 |
| WO | WO 92/16553 A1 | 10/1992 |
| WO | WO 93/16099 A2 | 8/1993 |
| WO | WO 97/28828 A1 | 8/1997 |
| WO | WO 98/24477 A1 | 6/1998 |
| WO | WO 99/45923 A1 | 9/1999 |
| WO | WO 00/18409 | 4/2000 |
| WO | WO 00/50079 | 8/2000 |
| WO | WO 01/85179 A2 | 11/2001 |
| WO | WO 02/57240 A1 | 7/2002 |
| WO | WO 02/100387 A1 | 12/2002 |
| WO | WO 03/000190 A2 | 1/2003 |
| WO | WO 2004/022078 A1 | 3/2004 |
| WO | WO 2004/039248 | 5/2004 |
| WO | WO 2005/000283 A2 | 1/2005 |
| WO | WO 2005/011689 A2 | 2/2005 |
| WO | WO 2005/049055 A1 | 6/2005 |
| WO | WO 2005/053795 A2 | 6/2005 |
| WO | WO 2005/110276 A1 | 11/2005 |
| WO | WO 2006/031376 A2 | 3/2006 |
| WO | WO 2007/121288 | 10/2007 |

OTHER PUBLICATIONS

Allali, F., et al., "Increase in Bone Mineral Density of Patients with Spondyloarthropathy Treated with Anti-tumour Necrosis Factor α," *Ann. Rheum. Dis.*, 62: 347-349 (2003).

Andonopoulos, A., et al., "Intra-articular Anti-tumor Necrosis Factor α Antibody in Recalcitrant Arthritis of Behcet's Disease," *Clinical and Experimental Rheumatology*, 21(4 Suppl 30): S57-S58 (Jul.-Aug. 2003).

Aoki, Y., et al., "Local Application of Disc-related Cytokines on Spinal Nerve Roots," *Spine*, 27(15): 1614-1617 (2002).

Arai, I., et al., "Pretreatment with Loxoprofen Sodium, 6-OHDA or Anti TNF-alpha Antibody Reduce Fos-like Immunoreactivity in Rat Experimental Lumber Disc Herniation," 111, *Abstracts of the 30th Annual Meeting of the International Society for the Study of the Lumbar Spine*, Vancouver, Canada (May 2003).

Ariga, K., et al., "Mechanical Stress-induced Apoptosis of Endplate Chondrocytes in Organ-cultured Mouse Intervertebral Discs," *Spine*, 28(14): 1528-1533 (2003).

Ashkenazi, A., et al., "Protection Against Endotoxic Shock by a Tumor Necrosis Factor Receptor Immunoadhesin," *Proc. Natl. Acad. Sci. USA*, 88: 10535-10539 (1991).

Awasthi, Y., et al., "Purification and Properties of Human Erythrocyte Glutathione Peroxidase," *J.Biol. Chem.*, 250(13): 5144-5149 (1975).

Baker, D., et al., "Control of Established Experimental Allergic Encephalomyelitis by Inhibition of Tumor Necrosis Factor (TNF) Activity Within the Central Nervous System Using Monoclonal Antibodies and TNF Receptor-immunoglobulin Fusion Proteins," *Eur. J. Immunol.*, 24: 2040-2048 (1994).

Benjamin, L., et al., "A Plasticity Window for Blood Vessel Remodelling is Defined by Pericyte Coverage of the Preformed Endothelial Network and is Regulated by PDGF-B and VEGF," *Development*, 125: 1591-1598 (1998).

Biemond, P., et al., "Protective Factors Against Oxygen Free Radicals and Hydrogen Peroxide in Rheumatoid Arthritis Synovial Fluid," *Arthritis Rheum.*, 27(7): 760-765 (1984).

Biskobing, D., "Novel Therapies for Osteoporosis," *Expert Opinion Invest. Drugs*, 12(4): 611-621 (2003).

Boehm, J., et al., "New Inhibitors of p38 Kinase," *Exp. Opin, Ther. Patents*, 10(1): 25-37 (2000).

Bokarewa, M., et al., "Local Infusion of Infliximab for the Treatment of Acute Joint Inflammation," *Ann. Rheum Dis.*, 62: 783-784 (2003).

Braun, J., et al., "Anti-tumour Necrosis Factor α Therapy for Ankylosing Spondylitis: International Experience," *Ann. Rheum. Dis.*, 61(Supp. III): iii51-iii60 (2002).

Braun, J., et al., "Overview of the Use of the Anti-TNF Agent Infliximab in Chronic Inflammatory Diseases," *Expert Opin. Biol. Ther.*, 3(1): 141-168 (2003).

Bringman, T., et al., "Monoclonal Antibodies to Human Tumor Necrosis Factors Alpha and Beta: Application for Affinity Purification, Immunoassays, and as Structural Probes," *Hybridoma*, 6(5): 489-507 (1987).

Brown, K., et al., "Gelatin/Chondroitin 6-sulfate Microspheres for the Delivery of Therapeutic Proteins to the Joint," *Arthritis. & Rheum.*, 41(12): 2185-2195 (1998).

Burke, J., et al., "Human Nucleus Pulposus Secretes Transforming Growth Factor Beta-1 and Basic Fibroblast Growth Factor," 189, *Abstracts of the 30th Annual Meeting of the International Society for the Study of the Lumbar Spine*, Vancouver, Canada (May 2003).

Burke, J., et al., "Intervertebral Discs Which Cause Low Back Pain Secrete High Levels of Proinflammatory Mediators," *J. Of Bone and Joint Surg. [Br]*, 84-B: 196-201 (2002).

Butler, D., et al., "TNF Receptor Fusion Proteins are Effective Inhibitors of TNF-mediated Cytotoxicity on Human KYM-1D4 Rhabdomyosarcoma Cells," *Cytokine*, 6(6): 616-623 (1994).

(56) References Cited

OTHER PUBLICATIONS

Capon, D., et al., "Designing CD4 Immunoadhesins for Aids Therapy," *Nature*, 337: 525-531 (1989).
Cardone, D., et al., "Diagnostic and Therapeutic Injection of the Hip and Knee," *Family Medicine*, 67(10): 2147-2152 (2003).
Castro, R., et al., "Failure of Bone Marrow Cells to Transdifferentiate Into Neural Cells in Vivo," *Science*, 297: 1299 (2002).
Čeponis, A., et al., "Effects of Low-dose, Noncytotoxic, Intraarticular Liposomal Clodronate on Development of Erosions and Proteoglycan Loss in Established Antigen-induced Arthritis in Rabbits," *Arthritis and Rheum.*, 44(8): 1908-1916 (2001).
Chae, H., et al., "The p38 Mitogen-activated Protein Kinase Pathway Regulates Interleukin-6 Synthesis in Response to Tumor Necrosis Factor in Osteoblasts," *Bone*, 28(1): 45-53 (2001).
Chan, J., et al., "Intraarticular Gene Transfer of TNFR:Fc Suppresses Experimental Arthritis with Reduced Systemic Distribution of the Gene Product," *Mol. Ther.*, 6(6): 727-736 (2002).
Cirillo, P., et al., "The Non-diaryl Heterocycle Classes of p38 MAP Kinase Inhibitors," *Current Topics in Medicinal Chemistry*, 2: 1021-1035 (2002).
CN 1 569 039 A (Niu X) Jan. 26, 2005 (abstract) World Patents Index [online]. London, GB: Derwent Publications, Ltd., Week 200577, Class B04, Accession No. 2005-749289.
CN 1 647 808 A (Zhou C) Aug. 3, 2005 (abstract) World Patents Index [online]. London, GB: Derwent Publications, Ltd., Week 200621, Class B04, Accession No. 2006-194507.
Connolly, J., et al., "Development of an Osteogenic Bone-marrow Preparation," *The Journal of Bone and Joint Surgery, Inc.*, 71-A(5): 684-691 (1989).
Conti, F., et al., "Successful Treatment with Intraarticular Infliximab for Resistant Knee Monarthritis in a Patient with Spondylarthropathy," *Arthritis & Rheumatism*, 52(4): 1224-1226 (2005).
Corcoran, A., et al., "Characterization of Ligand Binding by the Human p55 Tumour-necrosis-factor Receptor," *Eur. J. Biochem.*, 223: 831-840 (1994).
Cornefjord, M., et al., "Cerebrospinal Fluid Biomarkers in Experimental Spinal Nerve Root Injury," 38, *Abstracts of the 30th Annual Meeting of the International Society for the Study of the Lumbar Spine*, Vancouver, Canada (May 2003).
Crandall, C., "Combination Treatment of Osteoporosis: A Clinical Review," *J. of Women's Health & Gender-Based Medicine*, 11(3): 211-224 (2002).
Crevensten, G., et al., "Intervertebral Disc Cell Therapy for Regeneration: Mesenchymal Stem Cell Implantation in Rat Intervertebral Discs," *Ann. Biomed. Eng.*, 32(3): 430-434 (2004).
Dayer, J., "The Pivotal Role of Interleukin-1 in the Clinical Manifestations of Rheumatoid Arthritis," *Rheumatology*, Oxford University Press, London, GB, 42(Suppl 2): ii3-ii10 (2003).
Desai, S., et al., "Coated Microwell Plate-based Affinity Purification of Antigens," *Anal. Biochem.*, 328: 162-165 (2004).
DeSantis, A., et al., "Current and Emerging Therapies in Osteoporosis," *Expert Opin. Pharmacother.*, 3(7): 835-843 (2002).
Diwan, A., et al., "Current Concepts in Intervertebral Disk Restoration," *Tissue Engineering in Orthopedic Surgery*, 31(3): 453-464 (2000).
Edwards, S., et al., "Radiographic Assessment of Posterolateral Spine Fusion With and Without Platelet Rich Plasma," 117, *Abstracts of the 30th Annual Meeting of the International Society for the Study of the Lumbar Spine*, Vancouver, Canada (May 2003).
El-Khoury, G., et al., "Percutaneous Procedures for the Diagnosis and Treatment of Lower Back Pain: Diskography, Facet-joint Injection, and Epidural Injection," *AJR Am. J Roentgenol.*, 157(4): 685-691 (1991).
Engelmann, H., et al., "Two Tumor Necrosis Factor-binding Proteins Purified From Human Urine," *J. Biol. Chem.*, 265(3): 1531-1536 (1990).
Eustice, C., et al., "What is Viscosupplementation?" [online] ://arthritis.com/od/kneetreatments/g/viscosupplement_p.htm, Dec. 9, 2005>.
Ezra, A., et al., "Administration Routes and Delivery Systems of Bisphosphonates for the Treatment of Bone Resorption," *Adv. Drug Del. Rev.*, 42: 175-195 (2000).
Fendly, B., et al., "Murine Monoclonal Antibodies Defining Neutralizing Epitopes on Tumor Necrosis Factor," *Hybridoma*, 6: 359-370 (1987).
Földes, I., et al., "Trace Elements in Tissues of Normal and Vitamin $D_2$-treated Rats," *ACTA Biol. Acad. Sci. Hung.*, 26(3-4): 141-150 (1975).
Frain, J., et al., "Use of cDNA Microarrays to Investigate Cytokine Expression in Intervertebral Disc Degeneration," 126, *Abstracts of the 30th Annual Meeting of the International Society for the Study of the Lumbar Spine*, Vancouver, Canada (May 2003).
Gabay, C., "IL-1 Trap," *Curr. Opin. Invest. Drugs, Curr. Drugs*, London, GB, 4(5): 593-597 (2003).
Ganey, T., et al., "A Potential Role for Cell-based Therapeutics in the Treatment of Intervertebral Disc Herniation," *Eur. Spine J.*, 11(Suppl. 2): S206-S214 (2002).
Goodman, S., et al., "Effects of Local Infusion of TGFβ on Bone Ingrowth in Rabbit Chambers," *J. Biomed. Mat. Res. (Appl Biomater)*, 53: 475-479 (2000).
Gordon, J., et al., "Metalloproteinase Inhibitors as Therapeutics," *Clin. Exp. Rheumatol.*, 11(Suppl. 8): S91-S94 (1993).
Gori, A., et al., "Tumor Necrosis Factor-β Increased Production During Thalidomide Treatment in Patients With Tuberculosis and Human Immunodeficiency Virus Coinfection," *The Journal of Infectious Diseases*, 182: 639 (2000).
Goupille, P., et al., "Matrix Metalloproteinases: The Clue to Intervertebral Disc Degeneration?," *Spine*, 23(14): 1612-1626 (1998).
Guillen, C., et al., "The Effects of Local Administration of Lactoferrin on Inflammation in Murine Autoimmune and Infectious Arthritis," *Arthritis Rheum.*, 43(9): 2073-2080 (2000).
Haro, H., et al., "Matrix Metalloproteinase-7-dependent Release of Tumor Necrosis Factor-α in a Model of Herniated Disc Resorption," *J. Clin. Invest.*, 105(2): 143-150 (2000).
Hawks, D., "Alternative Medicine: Musculoskeletal System," *Clin. Tech. Small Anim. Pract.*, 17(1): 41-49 (2002).
Hayashida, K., et al., "Lactoferrin Enhances Peripheral Opioid-mediated Antinociception via Nitric Oxide in Rats," *Eur. J. Pharmacol.*, 484: 175-181 (2004).
Hayashida, K., et al., "Oral Administration of Lactoferrin Inhibits Inflammation and Nociception in Rat Adjuvant-induced Arthritis," *J. Vet. Med. Sci.*, 66(2): 149-154(2004).
Hirai, M., et al., "Production and Characterization of Monoclonal Antibodies to Human Tumor Necrosis Factor," *J. Immunol. Meth.*, 96: 57-62 (1987).
Hunter, C., et al., "Functional Behavior of Notochordal Cell Clusters in the Canine Nucleus Pulposus: Cell Communication and Survival," 70, *Abstracts of the 30th Annual Meeting of the International Society for the Study of the Lumbar Spine*, Vancouver, Canada (May 2003).
*Hydrogels*, Encyclopedia of Polymer Science and Technology, vol. 2, (Wiley and Sons, 2003).
Igarashi, A., et al., "Inflammatory Cytokines Release From Facet Joint Tissue in Degenerative Lumbar Disorders," 262, *Abstracts of the 30th Annual Meeting of the International Society for the Study of the Lumbar Spine*, Vancouver, Canada (May 2003).
Imai, Y., et al., "Effect of Recombinant Human Osteogenic Protein-1 on Extracellular Matrix Metabolism by Human Annulus Fibrosus and Nucleus Pulposus Cells," 205, *Abstracts of the 30th Annual Meeting of the International Society for the Study of the Lumbar Spine*, Vancouver, Canada (May 2003).
Imai, Y., et al., "The Quantification of Cytokine-induced Matrix Catabolism in Tissue Engeneered Intervertebral Discs," 67, *Abstracts of the 30th Annual Meeting of the International Society for the Study of the Lumbar Spine*, Vancouver, Canada (May 2003).
Inui, Y., et al., "Fas-ligand Expression on Nucleus Pulposus Cells Begins in Developing Embryo," 42, *Abstracts of the 30th Annual Meeting of the International Society for the Study of the Lumbar Spine*, Vancouver, Canada (May 2003).
Johnson, W., et al., "Collagenase Inhibitors: Their Design and Potential Therapeutic Use," *J. Enzyme Inhib.*, 2: 1-22 (1987).

(56) References Cited

OTHER PUBLICATIONS

Kamanh, A., et al., "Plasma Lipid Peroxidation and Antioxidant Levels in Patients with Rheumatoid Arthritis," *Cell Biochem. Funct.*, 22: 53-57 (2004).

Karppinen, J., et al., "Tumor Necrosis Factor-α Monoclonal Antibody, Infliximab, Used to Manage Severe Sciatica," *Spine*, 28(8): 750-754 (2003).

Kato, H., et al., "The Effect of IL-1 on the Rabbit Intervertebral Disc in Vivo," 199, *Abstracts of the 30th Annual Meeting of the International Society for the Study of the Lumbar Spine*, Vancouver, Canada (May 2003).

Kawakami, M., et al., "Possible Mechanism of Painful Radiculopathy in Lumbar Disc Herniation," *Clin. Orthop.*, 351: 241-251 (1998).

Kawakami, M., et al., "Role of IL-8, MCP-1 and PH in Neuropathic Pain Enhanced by Degenerative Nucleus Pulposus," 127, *Abstracts of the 30th Annual Meeting of the International Society for the Study of the Lumbar Spine*, Vancouver, Canada (May 2003).

Khot, A., et al, "The Use of Intradiscal Steroid Therapy for Lumbar Spinal Discogenic Pain—A Randomized Controlled Trial," *Spine*, 29(8): 833-837 (2004).

Kilic, B., et al., "Effects of Intra-articular Vitamin E and Corticosteroid Injection in Experimental Hemarthrosis in Rabbits," *Pediatr. Hematol. Oncol.*, 15(4): 339-346 (1998).

Kim, S., et al., "Ex Vivo Gene Delivery of IL-1Ra and Soluble TNF Receptor Confers a Distal Synergistic Therapeutic Effect in Antigen-induced Arthritis," *Mol. Ther.*, 6(5): 591-600 (2002).

Kimble, R., et al., "Estrogen Deficiency Increases the Ability of Stromal Cells to Support Murine Osteoclastogenesis Via an InterLeukin-1 and Tumor Necrosis Factor-mediated Stimulation of Macrophage Colony-stimulating Factor Production," *J. Biol. Chem.*, 271(46): 28890-28897 (1996).

Kimble, R., et al., "The Functional Block of TNF but Not of IL-6 Prevents Bone Loss in Ovariectomized Mice," *J. Bone Mm. Res.*, 12(6): 935-941 (1997).

Koch, H., et al., "Spontaneous Secretion of Interleukin 1 Receptor Antagonist (IL-1Ra) by Cells Isolated from Herniated Lumbar Discal Tissue After Discectomy," *Cytokine*, 10(9): 703-705 (1998).

Kolls, J., et al., "Prolonged and Effective Blockade of Tumor Necrosis Factor Activity Through Adenovirus-mediated Gene Transfer," *Proc. Natl. Acad. Sci. USA*, 91: 215-219 (1994).

Korhonen, T., et al., "Efficacy of Infliximab for Disc Herniation-induced Sciatica One-year Follow-up," 14, *Abstracts of the 30th Annual Meeting of the International Society for the Study of the Lumbar Spine*, Vancouver, Canada (May 2003).

Kozbor, D., et al., "The Production of Monoclonal Antibodies from Human Lymphocytes," *Immunol. Today*, 4(3): 72-79 (1983).

Kurz, B., et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10: 119-126 (2002).

Kwon, U., et al., "Dexamethasone Stimulates Cellular Proliferation While Downregulates Matrix Synthesis in Intervertebral Disc Cells," 29, *Abstracts of the 30th Annual Meeting of the International Society for the Study of the Lumbar Spine*, Vancouver, Canada (May 2003).

Lane, N., et al., "Basic Fibroblast Growth Factor Forms New Trabeculae that Physically Connect with Pre-existing Trabeculae, and This New Bone is Maintained With an Anti-resorptive Agent and Enhanced with an Anabolic Agent in an Osteopenic Rat Model," *Osteoporos. Int.*, 14: 374-382 (2003).

LaVan, D., et al., "Small-scale Systems for in Vivo Drug Delivery," *Nature Biotechnology*, 21(10): 1184-1191 (2003).

Le Maitre, C., et al., "Expression of the IL-1 Family in Human Intervertebral Disc," 217, *Abstracts of the 30th Annual Meeting of the International Society for the Study of the Lumbar Spine*, Vancouver, Canada (May 2003).

Le Maitre, C., et al., "Response of Human Intervertebral Disc Cells to IL-1," 216, *Abstracts of the 30th Annual Meeting of the International Society for the Study of the Lumbar Spine*, Vancouver, Canada (May 2003).

Le Visage, C., et al., "Interaction of Human Mescenchymal Stem Cells with Disc Cells: Changes in Biosynthesis of Extracellular Matrix," 25, *Abstracts of the 30th Annual Meeting of the International Society for the Study of the Lumbar Spine*, Vancouver, Canada (May 2003).

Lee, C., et al., "A Single Period of Hyperphysiologic Stretch Induces IL-6, TGF-beta and Cell Proliferation in Anulus Fibrosus Cells," 215, *Abstracts of the 30th Annual Meeting of the International Society for the Study of the Lumbar Spine*, Vancouver, Canada (May 2003).

Lee, J., et al., "Inhibition of p38 MAP Kinase as a Therapeutic Strategy," *Immunopharmacology*, 47: 185-201 (2000).

Lehman, T., et al., "Thalidomide Theraphy for Recalcitrant Systemic Onset Juvenile Rheumatoid Arthritis," *J. Pediatrics*, 140: 125-7 (2002).

Lesslauer, W., et al., "Recombinant Soluble Tumor Necrosis Factor Receptor Proteins Protect Mice From Lipopolysaccharide-induced Lethality," *Eur. J. Immunol.*, 21: 2883-2886 (1991).

Li, J., et al., "The Effects of Bone Morphogenetic Protein 2 (BMP-2) and Cartilage-derived Morphogentic Protein 2 (CDMP-2) on Aggrecan Gene Expression in Chondrocytes," 30, *Abstracts of the 30th Annual Meeting of the International Society for the Study of the Lumbar Spine*, Vancouver, Canada (May 2003).

Liang, C., et al., "Production and Characterization of Monoclonal Antibodies Against Recombinant Human Tumor Necrosis Factor/ Cachectin," *Biochem. Biophys. Res. Comm.*, 137: 847-854 (1986).

Loetscher, H., et al., "Molecular Cloning and Expression of the Human 55 kd Tumor Necrosis Factor Receptor," *Cell*, 61: 351-359 (1990).

Lotz, J., et al., "Cytokines in Normal, Degenerated, and Nucleoplasty-treated Porcine Discs," 157, *Abstracts of the 30th Annual Meeting of the International Society for the Study of the Lumbar Spine*, Vancouver, Canada (May 2003).

Lubberts, E., et al., "Intra-articular IL-10 Gene Transfer Regulates the Expression of Collagen-induced Arthritis (CIA) in the Knee and Ipsilateral Paw," *Clin. Exp. Immunol.*, 120: 375-383 (2000).

Maddipati, K., et al., "Characterization of the Major Hydroperoxide-reducing Activity of Human Plasma," *J. Biol. Chem.*, 262(36): 17398-17403 (1987).

Maeda, S., et al., "Changes With Age in Proteoglycan Synthesis in Cells Cultured in Vitro From the Inner and Outer Rabbit Annulus Fibrosus," *Spine*, 25(2): 166-169 (2000).

Marriott, J., et al., "CC-3052: A Water-soluble Analog of Thalidomide and Potent Inhibitor of Activation-induced TNF-α Production," *J. Immunol.*, 161: 4236-4243 (1998).

Martinez, J., et al., "Blood Platelet Glutathione Peroxidase: Some Properties and Partial Purification," *Thromb. Res.*, 19: 73-83 (1980).

McMillan, D., et al., "Intra-operative Autologous Blood Management," *Transfusion and Apheresis Science*, 27(1): 73-81 (2002).

Meager, A., et al., "Preparation and Characterization of Monoclonal Antibodies Directed Against Antigenic Determinants of Recombinant Human Tumour Necrosis Factor (rTNF)," *Hybridoma*, 6(3): 305-311 (1987).

Meijer, H., et al., "The Production of Anti-inflammatory Cytokines in Whole Blood by Physico-chemical Induction," *Inflamm. Res.*, 52: 404-407 (2003).

Miyamoto, H., et al., "The Effect of Mechanical Stress on the Production of Inflammatory Agents by Disc Cells," 110, *Abstracts of the 30th Annual Meeting of the International Society for the Study of the Lumbar Spine*, Vancouver, Canada (May 2003).

Möller, A., et al., "Monoclonal Antibodies to Human Tumor Necrosis Factor: In Vitro and in Vivo Application," *Cytokine*, 2(3): 162-169 (1990).

Molloy, T., et al., "The Roles of Growth Factors in Tendon and Ligament Healing," *Sports Med.*, 33(5): 381-394 (2003).

Moreira, A., et al., "Thalidomide Exerts Its Inhibitory Action on Tumor Necrosis Factor α by Enhancing mRNA Degradation," *J. Exp. Med.*, 177: 1675-1680 (1993).

Moroney, P., "PH and Anti-inflammatory Agents Modulate Nucleus Pulposus Cytokine Secretion," *The Spine Journal*, 2(5 Suppl): 49S-50S (2002) (abstract).

Muller, G., et al., "Amino-substituted Thalidomide Analogs: Potent Inhibitors of TNF-α Production," *Bioorg. Med. Chem. Lett.*, 9: 1625-1630 (1999).

(56) References Cited

OTHER PUBLICATIONS

Müller, R., "Determination of Affinity and Specificity of Anti-hapten Antibodies by Competitive Radioimmunoassay," *Meth. Enzymol.*, 92: 589-601 (1983).

Nakamura, K., et al., "Local Application of Basic Fibroblast Growth Factor into the Bone Increases Bone Mass at the Applied Site in Rabbits," *Arch. Orthop. Trauma Surg.*, 115: 344-346 (1996).

Nakamura, K., et al., "Stimulation of Endosteal Bone Formation by Local Intraosseous Application of Basic Fibroblast Growth Factor in Rats," *Rev. Rhum. [Engl. Ed.]*, 64(2): 101-105 (1997).

Niccoli, L., et al., "Intraarticular Injection of Infliximab in Relapsing Knee Effusion in Psoriatic Arthritis: A Pilot Study," *Ann. Rheum. Dis.*, 62(1): 239-240 (2003) and EULAR—Annual European Congress of Rheumatology, Lisbon, Portugal (2003) (abstract).

Nikas, S., et al., "Treatment of Resistant Rheumatoid Arthritis by Intra-articular Infliximab Injections: A Pilot Study," *Ann Rheum Dis.*, 63: 102-103 (2004).

Nikas, S., et al., "Treatment of Resistant Rheumatoid Arthritis by Intra-articular Injections with Infliximab: A Pilot Study," *Ann. Rheum. Dis.*, 62(1): 408 (2003) and EULAR—Annual European Congress of Rheumatology, Lisbon, Portugal (2003) (abstract).

Ohno, K., et al., "Transdiscal Lumbar Sympathetic Block: A New Technique for a Chemical Sympathectomy," *Anesth. Analg.*, 85: 1312-1316 (1997).

Ohtori, S., et al., "TNF-β and TNF-62 Receptor 1 Upregulation in GLIA and Neurons After Nerve Injury. Studies in Murine DRG and Spinal Cord," 13, *Abstracts of the 30th Annual Meeting of the International Society for the Study of the Lumbar Spine*, Vancouver, Canada (May 2003).

Ohtori, S., et al., "TNF-β-Deficient Mice Have Fewer Macrophages in Injured Nerve and Reduced Glial Activation in DRG and Spinal Cord," 250, *Abstracts of the 30th Annual Meeting of the International Society for the Study of the Lumbar Spine*, Vancouver, Canada (May 2003).

Okuma, M., et al., "Rotary Cell Culture System Stimulates Annulus Fibrosus Cell Proliferation but Suppresses Proteoglycan Metabolism," 164, *Abstracts of the 30th Annual Meeting of the International Society for the Study of the Lumbar Spine*, Vancouver, Canada (May 2003).

Olmarker, K., et al., "Selective Inhibition of Tumor Necrosis Factor-β Prevents Nucleus Pulposus-induced Thrombus Formation, Intraneural Edema, and Reduction of Nerve Conduction Velocity," *Spine*, 26(8): 863-869 (2001).

Pacifici, R., "Editorial: Cytokines, Estrogen, and Postmenopausal Osteoporosis—The Second Decade," *Endocrinology*, 139(6): 2659-2661 (1998).

Pargellis, C., et al., "Inhibition of p38 MAP Kinase by Utilizing a Novel Allosteric Binding Site," *Nature Structural Biology*, 9(4): 268-272 (2002).

Pederson, A., et al., "Thermal Assembly of a Biomimetic Mineral/Collagen Composite," *Biomaterials*, 24: 4881-4890 (2003).

Peppel, K., et al., "A Tumor Necrosis Factor (TNF) Receptor-IgG Heavy Chain Chimeric Protein as a Bivalent Antagonist of TNF Activity," *J. Exp. Med.*, 174: 1483-1489 (1991).

Raucci, A., et al., "Activation of the ERK1/2 and p38 Mitogen-activated Protein Kinase Pathways Mediates Fibroblast Growth Factor-induced Growth Arrest of Chondrocytes," *J. Biol. Chem.*, 279(3): 1747-1756 (2004).

Richardson, S., et al., "Human Bone Marrow Mesenchymal Stromal Cells as a Source of Chondrocytes for Treatment of Intervertebral Disc Degeneration," 27, *Abstracts of the 30th Annual Meeting of the International Society for the Study of the Lumbar Spine*, Vancouver, Canada (May 2003).

Risbud, M., et al., "Mesenchymal Stem Cells Respond to Their Microenvironment in Vitro to Assume Nucleus Pulposus-like Phenotype," 26, *Abstracts of the 30th Annual Meeting of the International Society for the Study of the Lumbar Spine*, Vancouver, Canada (May 2003).

Rodan, G., et al., "Therapeutic Approaches to Bone Diseases," *Science*, 289: 1508-1514 (2000).

Sakai, D., et al., "Autologous Transplantation of Mesenchymal Stem Cells for Disc Repair," 24, *Abstracts of the 30th Annual Meeting of the International Society for the Study of the Lumbar Spine*, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Salin, M., et al., "Free Radicals and Inflammation: Protection of Phagocytosing Leukocytes by Superoxide Dismutase," *J. Clin. Invest.*, 56: 1319-1323 (1975).

Sampaio, E., et aL., "Thalidomide Selectively Inhibits Tumor Necrosis Factor α Production by Stimulated Human Monocytes," *J. Exp. Med.*, 173: 699-703 (1991).

Schalkwijk, J., et aL., "Cationization of Catalase, Peroxidase, and Superoxide Dismutase," *J. Clin. Invest.*, 76: 198-205 (1985).

Schall, T., et al., "Molecular Cloning and Expression of a Receptor for Human Tumor Necrosis Factor," *Cell*, 61: 361-370 (1990).

Schatteman, L., et al., "Treatment of Refractory Inflammatory Monoarthritis in Ankylosing Spondylitis by Intraarticular Injection of Infliximab," *The Journal of Rheumatology*, 33: 182-85 (2006).

Shiel, W., "Ankylosing Spondylitis," MedicineNet.com [online], Sep. 2005 [retrieved on Jun. 20, 2006]. Retrieved from the Internet <URL: ://www.medicinenet.com/script/main/art.asp?articlekey=274&pf=3&pages=2>.

Sobajima, S., et al., "Stem Cell Therapy for Degenerative Disc Disease: An In-vitro Feasibility Study," 43, *Abstracts of the 30th Annual Meeting of the International Society for the Study of the Lumbar Spine*, Vancouver, Canada (May 2003).

Steer, J., et al., "Altered Leucocyte Trafficking and Suppressed Tumour Necrosis Factor α Release from Peripheral Blood Monocytes After Intra-articular Glucocorticoid Treatment," *Ann. Rheum. Dis.*, 57(12): 732-737 (1998).

Stepanik, T., et al., "Coisolation of Glutathione Peroxidase, Catalase and Superoxide Dismutase From Human Erythrocytes," *J. Biochem. Biophys. Methods*, 20: 157-169 (1990).

Stern, S., et al., "Human Intervertebral Disc Cell Culture for Disc Disorders," *Clin. Orthop.*, 419: 238-244 (2004).

Takada, T., et al., "IL-6 Production was Upregulated by Interaction Between Disc Tissue and Macrophages," 41, *Abstracts of the 30th Annual Meeting of the International Society for the Study of the Lumbar Spine*, Vancouver, Canada (May 2003).

Takegami, K., et al., "Osteogenic Protein-1 Enhances Matrix Replenishment by Intervertebral Disc Cells Previously Exposed to Interleukin-1," *Spine*, 27(12): 1318-1325 (2002).

Tanny, G., et al., "Improved Filtration Technique for Concentrating and Harvesting Bacteria," *Appl. Environ. Microbiol.*, 40(2): 269-273 (1980).

Teo, S., "Properties of Thalidomide and its Analogues: Implications for Anticancer Therapy," *AAPS Journal*, 7(1): E14-E19 (2005).

Tiku, M., et al., "Aggrecan Degradation in Chondrocytes is Mediated by Reactive Oxygen Species and Protected by Antioxidants," *Free Radic. Res.*, 30: 395-405 (1999).

Tiku, M., et al., "Evidence Linking Chondrocyte Lipid Peroxidation to Cartilage Matrix Protein Degradation," *J. Biol. Chem.*, 275(26): 20069-20076 (2000).

Tobinick, E., et al., "Perispinal TNF-alpha Inhibition for Discogenic Pain," *Swiss Med. Wkly.*, 133: 170-177 (2003).

Tobinick, E., "Targeted Etanercept for Discogenic Neck Pain: Uncontrolled, Open-label Results in Two Adults," *Clin. Thera.*, 25(4): 1211-1218 (2003).

Tobinick, E., "Targeted Etanercept for Treatment-refractory Pain Due to Bone Metastasis: Two Case Reports," *Clinical Therapeutics.*, 25(8): 2279-2288 (2003).

Tracey, K., et al., "Tumor Necrosis Factor in Metabolism of Disease: Hormonal Actions Versus Local Tissue Effects," *Nouv. Rev. Fr. Hematol.*, 34 Suppl: S37-42 (1992) (abstract).

Trif, M., et al., "Liposomes as Possible Carriers for Lactoferrin in the Local Treatment of Inflammatory Diseases," *Exp. Biol. Med.*, 226(6): 559-564 (2001).

Tsuji, T., et al., "Age-Related Changes in M-RNA Expression of Various Regulatory Factors in Rabbit Intervertebral Disc," 81,

(56) References Cited

OTHER PUBLICATIONS

*Abstracts of the 30th Annual Meeting of the International Society for the Study of the Lumbar Spine*, Vancouver, Canada (May 2003).
Vahle, J., et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3): 312-321 (2002).
Vukicevic, S., et al., "Induction of Nephrogenic Mesenchyme by Osteogenic Protein 1 (Bone Morphogenetic Protein 7)," *Proc. Natl. Acad. Sci.*, 93: 9021-9026 (1996).
Weiler, C., et al., "Expression of TNF-β in Autopsy and Biopsy Specimens of Intervertebral Discs of Various Age and Degeneration," 233, *Abstracts of the 30th Annual Meeting of the International Society for the Study of the Lumbar Spine*, Vancouver, Canada (May 2003).
Williams, A., et al., "Amelioration of Rat Antigen-induced Arthritis by Liposomally Conjugated Methotrexate is Accompanied by Downregulation of Cytokine mRNA Expression," *Rheumatology*, 40: 375-383 (2001).
Wittenberg, R., et al., "In Vitro Release of Prostaglandins and Leukotrienes from Synovial Tissue, Cartilage, and Bone in Degenerative Joint Diseases," *Arthritis & Rheumatism*, 36(10): 1444-1450 (Oct. 1993).
Xie, X., et al., "Treatment of Spondylodiscitis Intravenous Versus Percutaneous Intradiscal Applications of Antibiotics: An Experimental Study in Rabbits," 120, *Abstracts of the 30th Annual Meeting of the International Society for the Study of the Lumbar Spine*, Vancouver, Canada (May 2003).
Yabuki, S., et al., "Prevention of Compartment Syndrome in Dorsal Root Ganglia Caused by Exposure to Nucleus Pulposus," *Spine*, 26(8): 870-875 (2001).
Yaffe, A., et al., "Combined Local Application of Tetracycline and Bisphosphonate Reduces Alveolar Bone Resorption in Rats," *J. Periodontol.*, 74(7): 1038-1042 (2003).
Yang, J., et al., "Purification and Quantitation of a Rat Plasma Selenoprotein Distinct from Glutathione Peroxidase Using Monoclonal Antibodies," *J. Biol. Chem.*, 262(27): 13372-13375 (1987).
Yoon, S., et al., "LMP-1 Upregulates Proteoglycan Synthesis in Intervertebral Disc Cells Through a BMP Mediated Process," 31, *Abstracts of the 30th Annual Meeting of the International Society for the Study of the Lumbar Spine*, Vancouver, Canada (May 2003).
Zhang, C., et al., "Mitogen-activated Protein (MAP) Kinase Regulates Production of Tumor Necrosis Factor-β and Release of Arachidonic Acid in Mast Cells," *J. Biol. Chem.*, 272(20): 13397-13402 (1997).
Office Action (RR), U.S. Appl. No. 10/456,948, mailed Feb. 14, 2006.
Office Action, U.S. Appl. No. 10/456,948, mailed Aug. 29, 2006.
Final Office Action, U.S. Appl. No. 10/456,948, mailed Mar. 30, 2007.
Notice of Allowance, U.S. Appl. No. 10/456,948, mailed Jun. 29, 2007.
Notice of Allowance after RCE filed, U.S. Appl. No. 10/456,948, mailed Oct. 18, 2007.
Office Action (RR), U.S. Appl. No. 10/631,487, mailed Oct. 6, 2006.
Office Action, U.S. Appl. No. 10/631,487, mailed Jan. 29, 2007.
Final Office Action, U.S. Appl. No. 10/631,487, mailed Jul. 26, 2007.
Office Action, U.S. Appl. No. 10/631,487, mailed Mar. 10, 2008.
Office Action, U.S. Appl. No. 10/631,487, mailed Nov. 13, 2008.
Office Action, U.S. Appl. No. 10/631,487, mailed Jul. 20, 2009.
Final Office Action, U.S. Appl. No. 10/631,487, mailed Apr. 12, 2010.
Office Action (RR), U.S. Appl. No. 12/005,060, mailed Nov. 13, 2009.
Office Action, U.S. Appl. No. 12/005,060, mailed Mar. 31, 2010.
Final Office Action, U.S. Appl. No. 12/005,060, mailed Dec. 7, 2010.
Office Action (RR), U.S. Appl. No. 12/290,998, mailed Jun. 24, 2010.
Office Action, U.S. Appl. No. 12/290,998, mailed Sep. 30, 2010.

Ando, N., et al., "An Immunohistochemical Study of the Degenerative Lumbar Disc," *Orthopedics & Traumatology* 44(1): 176-178 (1995) (Published in Japanese with English Abstract), Abstract only.
Blight, A.R., "Miracles and molecules—progress in spinal cord repair," *Nature Neuroscience Supplement* 5:1051-1054 (Nov. 2002).
European Patent Office, Summons to attend oral proceedings pursuant to Rule 115(1) EPC, European Patent Application No. 04776014.5, dated May 20, 2010.
Muthumani, K., et al., "Suppression of HIV-1 viral replication and cellular pathogenesis by a novel p38/JNK kinase inhibitor," *AIDS* 18:730-748 (2004).
Abstract Yorimitsu, E., "A Comparative Study on the Pathological Changes of Intervertebral Discs after Intradiscal Injection of Various Kinds of Steroid Materials: An Experimental Study," *Journal Keio Medical Society* 74(5): 303-315 (1997) (Published in Japanese with English Abstract), Abstract only.
Communication, EP 10 183305, dated Dec. 29, 2010.
McIntyre, C.J., et al., "Pyridazine Based Inhibitors of p38 MAPK," *Bioorg. Med. Chem. Lett.* 12:689-692 (2002).
Rupert, K.C., et al., "Imidazopyrimidines, Potent Inhibitors of p38 MAP Kinase," *Bioorg. Med. Chem. Lett.* 13:347-350 (2003).
U.S. Appl. No. 12/290,998: Office Action dated Apr. 19, 2011.
Bertolini, D.R., et al., "Stimulation of Bone Resorption and Inihibition of Bone Formation in vitro by Human Tumour Necrosis Factors," *Nature*, 319:516-518 (1986).
Brandt, J., et al., "Successful Treatment of Active Ankylosing Spondylitis With the Anti-Tumor Necrosis Factor α Monoclonal Antibody Infliximab," *Arthritis & Rheumatism*, 43(6):1346-1352 (2000).
Brekke, O.H. and Sandlie, I, "Therapeutic Antibodies for Human Diseases at the Dawn of the Twenty-First Century," *Nature Reviews*, 2, 52-62 (2003).
Bullington, J. et al., "Inhibitors of Unactivated p38 MAP Kinase," *Bioorg. Med. Chem. Let.*, 16:6102-6106 (2006).
Centeno, C.J., et al., "Increased Knee Cartilage Volume in Degenerative Joint Disease Using Percutaneously Implanted, Autologous Mesenchymal Stem Cells," *Pain Phys.*, 11(3): 343-353 (2008).
Dernis, E., et al., "Infliximab in spondylarthropathy-influence on bone density," *Clin. Exp. Rheumatol.*, 20 (6 Suppl 28): S185-6 (2002).
Hayashi, Y., et al., "Direct Single Injection of p38 Mitogen-Activated Protein Kinase Inhibitor Does Not Affect Calcitonin Gene-Related Peptide Expression in Dorsal Root Ganglion Neurons Innervating Punctured Discs in Rats", *Spine*, 34(26): 2843-2847 (2009).
Höke, A., "Mechanisms of Disease: what factors limit the success of peripheral nerve regeneration in humans?" *Nature Clinical Practice Neurology*, 2(8): 448-454 (2006).
Hötten, et al., "Recombinant Human Growth Differentiation Factor 5 Stimulates Mesenchyme Aggregation and Chondrogenesis Responsible for the Skeletal Development of Limbs," *Growth Factors*, 13: 65-74 (1996).
Rheumatoid Arthritis, MedicineNet.com www.medicinenet.com/script/main-art.asp?articlekey=466&pf=38page=1 downloaded Apr. 22, 2011.
Van Beuningen, H.M., et al., "Differential Effects of Local Application of BMP-2 or TGF-B1 on Both Articular Cartilage Composition and Osteophyte Formation," *Osteoarthritis and Cartilage*, 6: 306-317 (1998).
Weinblatt, M.E., et al., "Adalimumab, A Fully Human Anti-Tumor Necrosis Factor Alpha Monoclonal Antibody, for the Treatment of Rheumatoid Arthritis in Patients Taking Concomitant Methotrexate," *Arthritis and Rheumatism*, 48(1), 35-45 (2003).
International Search Report in PCT/US2004/015285, mailed May 18, 2005, entitled "A Method of Treating Degenerative Disc Disease."
Written Opinion of the International Searching Authority in PCT/US2004/015285, mailed Nov. 18, 2005, entitled "A Method of Treating Degenerative Disc Disease."

(56) References Cited

OTHER PUBLICATIONS

International Preliminary Report on Patentability in PCT/US2004/015285 mailed Nov. 18, 2005, entitled "A Method of Treating Degenerative Disc Disease."

International Preliminary Report on Patentability in PCT/US2004/037500 mailed May 15, 2006, entitled "Autologous Treatment of Degenerated Disc With Cells."

Written Opinion in PCT/US2004/037500 mailed May 15, 2006, entitled "Autologous Treatment of Degenerated Disc With Cells."

International Search Report in PCT/US2004/037500 mailed Mar. 24, 2005, entitled "Autologous Treatment of Degenerated Disc With Cells."

Final Office Action in U.S. App. No. 11/881,926, dated Aug. 26, 2013, entitled "Transdiscal Administration of Specific Inhibitors of Pro-Inflammatory Cytokines."

Final Office Action in U.S. Appl. No. 12/290,998, dated Sep. 13, 2013, entitled "Transdiscal Administration of Anti-TNFa Antibodies and Growth Differentiation Factors."

* cited by examiner

TRANSDISCAL ADMINISTRATION OF SPECIFIC INHIBITORS OF PRO-INFLAMMATORY CYTOKINES

RELATED APPLICATIONS

This application is a continuation of U.S. application Ser. No. 11/881,926, filed Jul. 30, 2007, which is a Divisional of U.S. application Ser. No. 10/456,948, filed Jun. 6, 2003 now U.S. Pat. No. 7,344,716, which claims the benefit of U.S. Provisional Application No. 60/470,098, filed May 13, 2003. The entire teachings of the above applications are incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contained sulfated functional groups that retain water, thereby providing the nucleus pulposus within its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix (in particular, the MMPs (under mediation by the cytokines) begin cleaving the water-retaining portions of the proteoglycans, thereby reducing its water-retaining capabilities). This degradation leads to a less flexible nucleus pulposus, and so changes the load pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

Olmarker, *Spine* 26(8), 2001, pp. 863-9("Olmarker I") and Aoki, *Spine* 27(15), 2002, pp. 1614-17 teach that TNF-α appears to play a role in producing the pain associated with the nucleus pulposus contacting nerve roots of the spinal cord.

US Published Patent Application No. US 2003/0039651 ("Olmarker II") teaches a therapeutic treatment of nerve disorders comprising administration of a therapeutically effective dosage of at least two substances selected from the group consisting of TNF inhibitors (both specific and non-specific), IL-1 inhibitors, IL-6 inhibitors, IL-8 inhibitors, FAS inhibitors, FAS ligand inhibitors, and IFN-gamma inhibitors.

In the examples of Olmarker II, Olmarker II further teaches that these substances are to be administered through systemic pathways. In particular, Olmarker II teaches that "the major contribution of TNF-alpha may be derived from recruited, aggregated and maybe even extravasated leukocytes, and that successful pharmacologic block may be achieved only by systemic treatment. [0133]. Of note, Olmarker II appears to discourage the local addition of one therapeutic agent (doxycycline) to a transplanted nucleus pulposus. [0128].

PCT Published Patent Application No. WO 02/100387 ("Olmarker III") teaches the prevention of neovasculariation and/or neo-innervation of intervertebral discs by the administration of anti-angiogenic substances. Again, however, Olmarker III teaches systemic administration of these therapeutic agents.

U.S. Pat. No. 6,419,944 ("Tobinick") discloses treating herniated discs with cytokine antagonists, including infliximab. However, Tobinick teaches that local administration involves a subcutaneous injection near the spinal cord. Accordingly, Tobinick does not teach a procedure involving a sustained delivery of a drug for the treatment of DDD, nor directly administering a specific cytokine antagonist (such as infliximab) into the disc.

US Published Patent Application No. 2003/0049256 (Tobinick II) discloses that injection of such therapeutic molecules to the anatomic area adjacent to the spine is accomplished by interspinous injection, and preferably is accomplished by injection through the skin in the anatomic area between two adjacent spinous processes of the vertebral column.

Tobinick II further teaches that TNF antagonists may be administered by interspinous injection in the human and that the dosage level is in the range of 1 mg to 300 mg per dose, with dosage intervals as short as two days. Tobinick II further discloses that Interleukin-1 antagonists are administered in a therapeutically effective dose, which will generally be 10 mg to 200 mg per dose, and their dosage interval will be as short as once daily.

Tobinick, *Swiss Med. Weekly*, 2003, 133, 170-77 ("Tobinick III") teaches both perispinal and epidural administration of TNF inhibitors for spine related therapies.

Karppinen, *Spine*, 28(8), 203, pp. 750-4, teaches intravenously injecting or orally administering infliximab into patients suffering from sciatica.

As with Tobinick I and II, Karppinen does not teach a procedure involving a sustained delivery of a drug for the treatment of DDD, nor directly administering a specific cytokine antagonist (such as infliximab) into the disc.

U.S. Pat. No. 6,352,557 (Ferree) teaches adding therapeutic substances such as anti-inflammatory medications to morselized extra-cellular matrix, and injecting that combination into an interverterbral disc.

However many anti-inflammatory agents are non-specific and therefore may produce unwanted side effects upon other cells, proteins and tissue. In addition, the pain-reducing effect of these agents is typically only temporary. Lastly, these agents typically only relieve pain, and are neither curative nor restorative.

Alini, *Eur. Spine J.* 11(Supp.2), 2002, pp. S215-220, teaches therapies for early stage DDD, including injection of inhibitors of proteolytic enzymes or biological factors that stimulate cell metabolic activity (i.e., growth factors) in order to slow down the degenerative process. Alini I does not disclose inhibiting growth factors.

US Published Patent Application US 2002/0026244 ("Trieu") discloses an intervertebral disc nucleus comprising a hydrogel that may deliver desired pharmacological agents. Trieu teaches that these pharmacological agents may include growth factors such as TGF-B and anti-inflammatory drugs, including steroids. Trieu further teaches that these pharmacological agents may be dispersed within the hydrogel having an appropriate level of porosity to release the pharmacological agent at a desired rate. Trieu teaches that these agents may be released upon cyclic loading or upon resorption.

Takegami, Spine, 27(12), 2002, 1318-25 teaches that injecting TGF-B into the disc space results in enhanced replenishment of the extracellular matrix damaged by cytokines. Takegami further teaches that the half-life of a growth factor injected into the interveterbal disc can be expected to be longer than that injected into a synovial joint because the nucleus pulposus is surrounded by the fibrous structure of the annulus fibrosus, thus providing a confined environment. Diwan, Tissue Engineering in Orthopedic Surgery, 31(3) July 2000, pp. 453-464, reports on another Takegami paper that concluded that a delivery system allowing prolonged delivery (>3 days) would have to be used to obtain the observed effect of the growth factor.

Alini, Spine 2003 28(5), pp. 446-54, discloses a cell seeded collagen-hyaluronan scaffold supplemented with growth factors such as TGF-B, bFGF, and IGF-1 for use in regenerating a nucleus pulposus.

Maeda et al. Spine 2000, 25(20 pp. 166-169, 2000 reports on the in vitro response to interleukin-1 receptor antagonist protein (IRAP) of rabbit annulus fibrosus exposed to IL-1. Maeda suggests that IRAP could be useful in inhibiting the degradation of the disc.

Yabuki, Spine, 2001, 26(8), 870-5, teaches the use of an anti-TNF drug for the treatment of sciatica.

U.S. Pat. No. 6,277,969 ("Le") discloses the use of anti-TNF antibodies for therapy of TNF-mediated pathologies. Le teaches parental administration of the antibodies.

In sum, when investigators suggest the administration of specific TNF-a inhibitors or specific interleukin inhibitors, the investigators appear not only to teach only the administration of those therapeutics to tissue outside the disc, but it also appears to discourage the trans-discal administration of therapeutic substances.

SUMMARY OF THE INVENTION

The present inventors have developed a number of procedures for efficaciously treating degenerative disc disease by drug therapy.

The present inventors have noted that although Tobinick, Olmarker and Karppinenen taught the therapeutic use of pro-inflammatory cytokine-antagonist monoclonal antibodies in treating sciatica, each of these investigators targeted tissue outside of the disc.

In accordance with the present invention, the present inventors have developed a method of treating an intervertebral disc in which a high specificity inhibitor of a pro-inflammatory cytokine is administered transdiscally (i.e., the target tissue is a degenerating disc).

There are believed to be several advantages to directly administering these therapeutic inhibitors to a targeted disc over the treatments disclosed by Tobinick and Karppinenen:

First, since it is known that many cytokines (such as interleukins and TNF-α) also play roles in mediating the degradation of the extracellular matrix (ECM) of the nucleus pulposus, injecting an antagonist or inhibitor of these proteins directly into the disc prevents the target cytokine from inducing any further ECM degradation. In effect, the transdiscal administration of the cytokine antagonist arrests the aging process of the degenerating disc. Accordingly, the present invention seeks to treat the degenerative disc at a much earlier stage of DDD than Tobinick and Karppinenen and thereby prevents degradation of the ECM.

Second, it is further known that nerve ending nociceptors are present within the annulus fibrosus, and that cytokines such as TNF irritate nerves. It is believed that injecting an anti-TNF antagonist into the disc space also prevents the TNF from causing nerve irritation within the disc. Thus, the pain attributed to irritation of these nerves can be efficiently eliminated.

Third, since the annulus fibrosus portion of the disc comprises a relatively dense fibrous structure, this outer component of the disc may provide a suitable depot for the high specificity cytokine antagonist (HSCA), thereby increasing its half-life in the disc.

Fourth, since the high specificity antagonist inhibits only the specific cytokine of interest, the HSCA may be combined with other therapeutic agents (such as TGF-B, or mesenchymal stem cells) that can also be injected into the disc without reducing the effectiveness of those agents.

Fifth, since it is believed that many of the problematic cytokines are actually secreted by either nucleus pulposus or annulus fibrosus cells, transdiscal injection of the high specificity antagonists will advantageously attack the problematic cytokines at their source of origination.

Accordingly, in a first aspect of the present invention, there is provided a method of treating an intervertebral disc having a nucleus pulposus, comprising the steps of:

a) transdiscally administering a formulation comprising a high specificity cytokine antagonist (HSCA) into an intervertebral disc.

DETAILED DESCRIPTION OF THE INVENTION

A description of preferred embodiments of the invention follows.

For the purposes of the present invention, the terms "inhibitor" and "antagonist" are used interchangeably. A protein may be inhibited at the synthesis level, at the translation level, by shedding, by antibodies, or by soluble receptors. The term "patient" refers to a human having a degenerating disc.

For the purposes of the present invention "Transdiscal administration" includes, but is not limited to:

a) injecting a formulation into the nucleus pulposus of a degenerating disc, preferably a relatively intact degenerating disc, b) injecting a formulation into the annulus fibrosus of a degenerating disc, preferably relatively intact degenerating disc, c) providing the formulation in a patch attached to the outer wall of the annulus fibrosus, d) providing the formulation in a depot at a location outside but closely closely adjacent the outer wall of the annulus fibrosus (hereinafter, "trans-annular administration".

e) providing the formulation in a depot at a location outside but closely adjacent the endplates of the adjacent vertebral bodies (hereinafter, "trans-endplate administration".

Because DDD is a continuous process, the degenerating disc to which the therapeutic drug is administered may be in any one of a number of degenerative states. Accordingly, the degenerating disc may be an intact disc. The degenerating disc may be a herniated disc (wherein a portion of the annulus fibrosus has a bulge). The degenerating disc may be a ruptured disc (i.e., wherein the annulus fibrosus has ruptured and bulk nucleus pulposus has exuded). The degenerating disc may be delaminated (wherein adjacent layers of the annulus fibrosus have separated). The degenerating disc may have fissures (wherein the annulus fibrosus has fine cracks or tears through which selected molecules from the nucleus pulposus can leak).

The present invention is directed to providing directly through a diseased intervertebral disc at least one highly specific cytokine antagonist capable of specifically inhibiting a cytokine (preferably, a pro-inflammatory cytokine) present in the disc. Preferably, the HSCA inhibits the action of a specific pro-inflammatory cytokine released by disc cells or by invading macrophages during the degenerative process.

In some embodiments, the antagonist is capable of specifically inhibiting a pro-inflammatory cytokine selected from the group consisting of TNF-α, an interleukin (preferably, IL-1, Il-6 and IL-8), phospholipase A2 (PLA2), FAS, an FAS ligand, and IFN-gamma. Such specific inhibitors include those identified on pages 5-18 of Olmarker II, the specification of which is incorporated by reference in its entirety.

In some embodiments, the HSCA inhibits the cytokine by preventing its production. In some embodiments, the HSCA inhibits the cytokine by binding to a membrane-bound cytokine. In others, the HSCA inhibits the cytokine by binding to a solubilized cytokine. In some embodiments, the HSCA inhibitor inhibits the cytokine by both binding to membrane bound cytokines and to solubilized cytokine. In some embodiments, the HSCA is a monoclonal antibody ("mAb"). The use of mAbs is highly desirable since they bind specifically to a certain target protein and to no other proteins. In some embodiments, the HSCA inhibits the cytokine by binding to a natural receptor of the target cytokine.

In some embodiments, the HSCA inhibits the cytokine by preventing its production. One example thereof is an inhibitor of p38 MAP kinase. In some embodiments, the TNF inhibitor inhibits the TNF by binding to membrane bound TNF in order to prevent its release from membrane. In others, the TNF inhibitor inhibits the TNF by binding to solubilized TNF. One example thereof is etanercept. In some embodiments, the TNF inhibitor inhibits the TNF by both binding to membrane bound TNF and to solubilized TNF. One example thereof is infliximab. In some embodiments, the HSCA inhibits the cytokine by binding to a natural receptor of the target cytokine.

Preferred TNF antagonists include, but are not limited to the following: etanercept (Enbrel®-Amgen); infliximab (Remicade®-Johnson and Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); and onercept, a recombinant TNF binding protein (r-TBP-1) (Serono).

TNF antagonists suitable for compositions, combination therapy, co-administration, devices and/or methods of the present invention (further comprising at least one anti body, specified portion and variant thereof, of the present invention), include, but are not limited to, anti-TNF antibodies (e.g., at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, enteracept (Enbrel™), adalimulab (Humira™), CDP-571, CDP-870, afelimomab, lenercept, and the like), antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signaling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-specificity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the specificity constant of chimeric antibody cA2 was calculated to be $1.04 \times 10^{10} M^{-1}$. Preferred methods for determining monoclonal antibody specificity and specificity by competitive inhibition can be found in Harlow, et al., *antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2000); Kozbor et al., *Immunol. Today*, 4:72-79 (1983); Ausubel et al., eds. *Current Protocols in Molecular Biology*, Wiley Interscience, New York (1987-2000); and Muller, *Meth. Enzymol.*, 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943, 852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., Biochem. Biophys. Res. Comm. 137:847-854 (1986); Meager, et al., Hybridoma 6:305-311 (1987); Fendly et al., Hybridoma 6:359-369 (1987); Bringman, et al., Hybridoma 6:489-507 (1987); and Hirai, et al., J. Immunol. Meth. 96:57-62 (1987), which references are entirely incorporated herein by reference).

Preferred TNF receptor molecules useful in the present invention are those that bind TNFa with high specificity (see, e.g., Feldmann et al., International Publication No. WO 92/07076 (published Apr. 30, 1992); Schall et al., Cell 61:361-370 (1990); and Loetscher et al., Cell 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., Eur. J Biochem. 223:831-840 (1994)), are also useful in the present invention. Truncated forms of the TNF receptors, comprising the ECD, have been detected in urine and serum as 30 kDa and 40 kDa TNFa inhibitory binding proteins (Engelmann, H. et al., J Biol. Chem. 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high specificity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., Eur. J. Immunol. 21:2883-2886 (1991); Ashkenazi et al., Proc. Natl. Acad. Sci. USA 88:10535-10539 (1991); Peppel et al., J Exp. Med. 174:1483-1489 (1991); Kolls et al., Proc. Natl. Acad. Sci. USA 91:215-219 (1994); Butler et al., Cytokine 6(6):616-623 (1994); Baker et al., Eur. J. Immunol. 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., Nature 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high specificity and possess low immunogenicity). A functional equivalent of TNF receptor molecule also includes modified TNF receptor molecules that functionally resemble TNF receptor molecules that can be used in the present invention (e.g., bind TNFα with high specificity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., Current Protocols in Molecular Biology, Greene Publishing Assoc. and Wiley-Interscience, New York (1987-2003).

In some embodiments, the monoclonal antibody that inhibits TNF-a is selected from the group consisting of monoclonal rodent-human antibodies, rodent antibodies, human antibodies or any portions thereof, having at least one antigen binding region of an immunoglobulin variable region, which antibody binds TNF. Preferably, this monoclonal antibody is selected from the group of compounds disclosed in U.S. Pat. No. 6,277,969, the specification of which is incorporated by reference. In some embodiments, the infliximab is delivered in a formulation having an infliximab concentration of between about 30 mg/ml and about 60 mg/ml.

In some embodiments, the specific inhibitor of TNF-a is an inhibitor of p38 MAP kinase, preferably, a small molecule inhibitor of $p_{38}$ MAP kinase. The inhibition of $p_{38}$ MAP kinase is believed to block production of both TNF-a and Il-2, both of which are pro-inflammatory cytokines. The small molecule inhibitors of p38 MAP kinase are very specific & potent (~nM). Without wishing to be tied to a theory, it is believed that inhibition of p38 should not block TGF signaling nor TGF activity. It is further believed that p38 inhibitors may also block induction of some metalloproteinases, COX 2 and NO synthetase. It is further believed that P38 inhibitors do not inhibit interleukins involved in immune cell proliferation such as IL-2.

In some embodiments, the HSCA is a specific antagonist of an interleukin. Preferably, the target interleukin is selected from the group consisting IL-1, IL-2, IL-6 and IL-8, and IL-12. Preferred antagonists include but are not limited to Kineretg (recombinant IL 1-RA, Amgen), IL1-Receptor Type 2 (Amgen) and IL-1 Trap (Regeneron).

The present inventors note that DDD involves the progressive degeneration of a disc in which many factors are involved. In many of these instances, simply providing a single dose or even a regimen over the space of a few days may not be sufficient to resolve the DDD. For example, if DDD were caused in part by mechanical instability in a functional spinal unit, then simply providing a one-time therapy for the disc cells will likely only delay the onset of the DDD. Therefore, there is a need to provide a long-term drug therapy treatment of DDD that does not require multiple injections.

Because it is believed that the cytokines of interest both produce pain and degrade the ECM when present within the nucleus pulposus, it is desirable for the HSCA to remain within the nucleus pulposus as long as possible in a pharmaceutically effective amount. The half-life of the HSCA within the nucleus pulposus will depend upon many factors, including the size of the HSCA and its charge. In general, the larger the molecular weight of the HSCA, the more likely it is to remain contained by the annulus fibrosus portion of the disc.

If the half-life of the HSCA is relatively short, then it would be desirable for a relatively large dose of the HSCA to be administered into the disc. In this condition, quick depletion of the HSCA would not cause the HSCA to fall below therapeutically effective levels until an extended period.

Although a large dose of the HSCA would be desirable in such instances, it is also known that nociceptors present on the inner wall of the annulus fibrosus react to increased pressure and produce pain, and that one avenue for increasing the pressure in the nucleus pulposus is to inject a critical volume of water. In some cases, the added amount could be as little as one cc by volume to produce pain. Accordingly, if a dilute concentration of an HSCA is added to the nucleus pulposus to provide a large dose, the resulting pressure increase caused by this added volume could be sufficient to cause acute pain.

For example, if it were determined that 100 mg of an HSCA was needed to therapeutically effect a nucleus pulposus, and that HSCA was provided in concentrations of 30-60 mg/ml, then at least 1.5 ml of the HSCA would need to be injected into the nucleus pulposus in order to provide the desired therapeutic effect. However, when injecting volumes into the nucleus pulposus, it is desirable that the volume of drug delivered be no more than 1 ml, preferably no more than 0.5 ml, more preferably between 0.1 and 0.3 ml. When injected in these smaller quantities, it is believed the added volume will not cause an appreciable pressure increase in the nucleus pulposus.

In contrast, Olmarker mixed 100 µl of a formulation comprising only 1.11 mg/ml of a monoclonal antibody into 40 mg of an extracted nucleus pulposus.

Accordingly, in some embodiments, the concentration of the TNF-a antagonist in the administered drug is at least 100 mg/ml. When 100 mg of the HSCA is needed to produce the desired therapeutic result, no more than 1 ml of the drug need be injected. Preferably, the concentration of the TNF-a antagonist in the administered drug is at least 200 mg/ml. In this condition, no more than 0.5 ml of the drug need be injected. Preferably, the concentration of the TNF-a antagonist in the administered drug is at least 500 mg/ml. In this condition, between 0.03 and 0.3 ml of the drug need be injected.

In some embodiments, the HSCA is provided in a sustained release device. The sustained release device is adapted to remain within the disc for a prolonged period and slowly release the HSCA contained therein to the surrounding environment. This mode of delivery allows an HSCA to remain in therapeutically effective amounts within the disc for a prolonged period.

In some embodiments, the HSCA is predominantly released from the sustained delivery device by its diffusion through the sustained delivery device (preferably, though a polymer). In others, the HSCA is predominantly released from the sustained delivery device by the biodegradation of the sustained delivery device (preferably, biodegradation of a polymer).

Preferably, the sustained release device comprises a bioresorbable material whose gradual erosion causes the gradual release of the HSCA to the disc environment. In some embodiments, the sustained release device comprises a bioresorbable polymer. Preferably, the bioresorbable polymer has a half-life of at least one month, more preferably at least two months, more preferably at least 6 months.

In some embodiments, the sustained release device provides controlled release. In others, it provides continuous release. In others, it provides intermittent release. In others, the sustained release device comprises a biosensor.

In some embodiments, the sustained delivery device comprises bioerodable macrospheres. The HSCA is preferably contained in a gelatin (or water or other solvent) within the capsule, and is released to the disc environment when the outer shell has been eroded. The device can include a plurality of capsules having outer shells of varying thickness, so that the sequential breakdown of the outer shells provides periodic release of the HSCA.

In some embodiments, the sustained delivery device comprises an inflammatory-responsive delivery system, preferably comprising bioerodable microspheres that are eroded by invading macrophages. This technology provides a high correspondence between physiologic inflammation of disc environment and the release of the HSCAs into that environment. Preferably, the technology disclosed in Brown et al., *Arthritis. Rheum.* 1998 December; 41(12) pp., 2185-95 is selected.

In some embodiments, the sustained delivery device comprises the devices disclosed in U.S. Pat. No. 5,728,396 ("Peery"), the specification of which is incorporated by reference in its entirety.

In some embodiments, the sustained delivery device comprises a plurality (preferably at least one hundred) of water-containing chambers, each chamber containing the HSCA. Each chamber is defined by bilayer lipid membranes comprising synthetic duplicates of naturally occurring lipids. The release of the drug can be controlled by varying at least one of the aqueous excipients, the lipid components, and the manufacturing parameters. Preferably, the formulation comprises no more than 10% lipid. In some embodiments, the Depofoam™ technology of Skyepharma PLC (located in London, United Kingdom) is selected.

In some embodiments, the sustained delivery device comprises a delivery system disclosed in U.S. Pat. No. 5,270,300 ("Hunziker"), the specification of which is incorporated by reference in its entirety.

In some embodiments, the sustained delivery device comprises the co-polymer poly-DL-lactide-co-glycolide (PLG). Preferably, the formulation is manufactured by combining the HSCA, the co-polymer and a solvent to form a droplet, and then evaporating the solvent to form a microsphere. The plurality of microspheres are then combined in a biocompatible diluent. Preferably, the HSCA is released from the co-polymer by its diffusion therethrough and by the biodegradation of the co-polymer. In some embodiments hereof, the ProLease™ technology of Alkermes (located in Cambridge, Mass.) is selected.

Hydrogels can also be used to deliver the HSCA is a time-release manner to the disc environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the HSCA at the application site, thereby eliminating undesired migration from the disc. The hydrogels are also biocompatible, e.g., not toxic, to cells suspended in the hydrogel.

A "hydrogel-HSCA composition" is a suspension of a hydrogel containing desired HSCA. The hydrogel-HSCA composition forms a uniform distribution of HSCA with a well-defined and precisely controllable density. Moreover, the hydrogel can support very large densities of HSCA. In addition, the hydrogel allows diffusion of nutrients and waste products to, and away from, the HSCA, which promotes tissue growth.

Hydrogels suitable for use in the present invention include water-containing gels, i.e., polymers characterized by hydrophilicity and insolubility in water. See, for instance, "Hydrogels", pages 458-459 in Concise Encyclopedia of Polymer Science and Engineering, Eds. Mark et al., Wiley and Sons, 1990, the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels can:
 a) house viable cells, such as mesenchymal stems cells, and
 b) assist with load bearing capabilities of the disc.

In a preferred embodiment, the hydrogel is a fine, powdery synthetic hydrogel. Suitable hydrogels exhibit an optimal combination of such properties as compatibility with the matrix polymer of choice, and biocompatability. The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL, and mixtures thereof.

If the half-life of the HSCA within the disc is relatively long, then it may be assumed that a relatively small dose of the HSCA can be administered into the disc. In this condition, the slow depletion of the HSCA would not cause the HSCA to fall below therapeutically effective levels in the disc until an extended period of time has elapsed.

In some embodiments in which HSCAs have long half-lives within the disc, the dose administered can be very small.

For example, if it is believed that an HSCA is effective when present in the range of 1-10 mg/kg or 1-10 ppm (as is believed to be the case for the TNF antagonist Remicade™), and since a typical nucleus pulposus of a disc has a volume of about 3 ml (or 3 cc, or 3 g), then only about 3-30 ug of the HSCA need be administered to the disc in order to provide a long lasting effective amount of the drug. As a point of reference, Tobinick discloses that at least 1 mg of cytokine antagonist should be administered perispinally in order to cure back pain. Similarly, Olmarker mixed 100 ml of a formulation comprising 1.11 mg/ml of a monoclonal antibody into 40 mg of an extracted nucleus pulposus, thereby producing a monoclonal antibody concentration of about 3 parts per thousand. The smaller amounts available by this route reduce the chances of deleterious side effects of the HSCA.

For example, suppose a clinician administered 0.3 ml of 60 mg/ml infliximab into a 2.7 cc disc, thereby producing a infliximab concentration in the disc of about 6 mg/ml, or 6 parts per thousand. Without wishing to be tied to a theory, if infliximab has the same half-life within a nucleus pulposus as it does when administered systemically (i.e., about 1 week), then the concentration of infliximab would remain above about 10 ppm for about 9 weeks. Therefore, if another dose were needed, the clinician would only need to provide the second dose after about two months.

Therefore, in some embodiments, the HSCA is provided in a dose of less than 1 mg, preferably, less than 0.5 mg, more preferably, less than 0.1 mg, more preferably less than 0.01 mg. The smaller amounts available by this route reduce the chances of deleterious side effects of the HSCA. Preferably, the HSCA provided in these smaller amounts is a TNF antagonist, more preferably is infliximab.

In preferred embodiments, the formulation of the present invention is administered directly into the disc through the outer wall of the annulus fibrosus. More preferably, the direct administration includes depositing the HSCA in the nucleus pulposus portion of the disc. In this condition, the fibrous nature of the annulus fibrosus that surrounds the nucleus pulposus will help keep the HSCA contained within the disc.

Preferably, the formulation of the present invention is injected into the disc through a small bore needle. More preferably, the needle has a bore of 22 gauge or less, so that the possibilities of producing a herniation are mitigated. More preferably, the needle has a bore of 24 gauge or less, so that the possibilities of producing a herniation are even further mitigated.

If the volume of the direction injection of the formulation is sufficiently high so as to cause a concern of overpressurizing the nucleus pulposus, then it is preferred that at least a portion of the nucleus pulposus be removed prior to direct injection. Preferably, the volume of removed nucleus pulposus is substantially similar to the volume of the formulation to be injected. More preferably, the volume of removed nucleus pulposus is within 80-120% of the volume of the formulation to be injected. In addition, this procedure has the added benefit of at least partially removing some degenerated disc from the patient.

In other embodiments, the formulation is delivered into the disc space through the endplate of an opposing vertebral body. This avenue eliminates the need to puncture the annulus fibrosus, and so eliminates the possibility of herniation.

Although the cytokine antagonists may therapeutically treat the disc by binding the target cytokine, and thereby reducing pain and arresting degradation of the ECM, it is believed that at least some of these antagonists do not help repair the damage done by the cytokine to the ECM.

Therefore, there may be a need to provide a therapy that also helps repair the ECM.

In accordance with the present invention, there is provided a method of treating degenerative disc disease in an intervertebral disc having a nucleus pulposus, comprising the steps of:
 a) administering a highly specific cytokine antagonist into a degenerating disc; and
 b) administering a second therapeutic agent in an amount effective to at least partially repair the disc.

In accordance with one aspect of the invention, both the HSCA and second therapeutic agent are locally administered into the disc. Because the HSCA is specific, it does not interfere with the locally administered second therapeutic agent, and so each agent may independently work to provide therapy to the diseased disc.

In some embodiments, the HSCA and second therapeutic agent are administered simultaneously. In others, the HSCA is administered first. In still others, the second therapeutic agent is administered first.

Other compounds which may be added to the disc include, but are not limited to: vitamins and other nutritional supplements; hormones; glycoproteins; fibronectin; peptides and proteins; carbohydrates (both simple and/or complex); proteoglycans; oligonucleotides (sense and/or antisense DNA and/or RNA); BMPs; antibodies (for example, to infectious agents, tumors, drugs or hormones); and gene therapy reagents. Genetically altered cells and/or other cells may also be included in the matrix of this invention. If desired, substances such as pain killers and narcotics may also be admixed with a polymer for delivery and release to the disc space.

Preferably, healthy cells are introduced into the disc that have the capability of at least partially repairing any damage done to the disc during the degenerative process. In some embodiments, these cells are introduced into the nucleus pulposus and ultimately produce new extracellular matrix for the nucleus pulposus. In others, these cells are introduced into the annulus fibrosus and produce new extracellular matrix for the annulus fibrosus.

In some embodiments, these cells are obtained from another human individual (allograft), while in others, the cells are obtained from the same individual (autograft). In some embodiments, the cells are taken from an intervertebral disc (and can be either nucleus pulposus cells or annulus fibrosus cells), while in others, the cells are taken from a non-disc tissue (and may be mesenchymal stem cells). In others, autograft chondrocytes (such as from the knee, hip, shoulder, finger or ear) may be used.

Preferably, when viable cells are selected as the second therapeutic substance, the viable cells comprise mesenchymal stem cells (MSCs). MSCs provide a special advantage for administration into a degenerating disc because it is believed that they can more readily survive the relatively harsh environment present in the degenerating disc; that they have a desirable level of plasticity; and that they have the ability to proliferate and differentiate into the desired cells.

In some embodiments, the mesenchymal stems cells are obtained from bone marrow, preferably autologous bone marrow. In others, the mesenchymal stems cells are obtained from adipose tissue, preferably autologous adipose tissue.

In some embodiments, the mesenchymal stem cells injected into the disc are provided in an unconcentrated form. In others, they are provided in a concentrated form. When provided in concentrated form, they are preferably uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated by reference in its entirety, are preferably used. In some preferred embodiments, the matrix used to filter and concentrate the MSCs is also administered into the nucleus pulposus. If this matrix has suitable mechanical properties, it can be used to restore the height of the disc space that was lost during the degradation process.

As used herein, the term "growth factors" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and -2) and FGF-4, members of the platelet-derived growth factor (PDGF) family, including PDGF-AB, PDGF-BB and PDGF-AA; EGFs, members of the insulin-like growth factor (IGF) family, including IGF-I and -II; the TGF-0 superfamily, including TGF-β1, 2 and 3 (including MP-52), osteoid-inducing factor (OIF), angiogenin(s), endothelins, hepatocyte growth factor and keratinocyte growth factor; members of the bone morphogenetic proteins (BMP's) BMP-1, (BMP-3); BMP-2; OP-1; BMP-2A, -2B, and -7, BMP-14; HBGF-1 and -2; growth differentiation factors (GDF's), members of the hedgehog family of proteins, including indian, sonic and desert hedgehog; ADMP-1; members of the interleukin (IL) family, including IL-1 thru -6; GDF-5 and members of the colony-stimulating factor (CSF) family, including CSF-1, G-CSF, and GM-CSF; and isoforms thereof.

In some embodiments, the growth factor is selected from the group consisting of TGF-B, bFGF, and IGF-1. These growth factors are believed to promote regeneration of the nucleus pulposus. Preferably, the growth factor is TGF-B. More preferably, TGF-B is administered in an amount of between 10 ng/ml and 5000 ng/ml, more preferably between 50 ng/ml and 500 ng/ml, more preferably between 100 ng/ml and 300 ng/ml.

In some embodiments, platelet concentrate is provided as the second therapeutic agent. Preferably, the growth factors released by the platelets are present in an amount at least two-fold (more preferably, four-fold) greater than the amount found in the blood from which the platelets were taken. More preferably, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

Since it is known that many pro-inflammatory proteins play a role in disc degeneration, and that the antagonists of the present invention are highly specific, it is further believed that injecting at least two of the highly specific antagonists of the present invention directly into the disc would be advantageous.

Therefore, in accordance with the present invention, there is provided a method of treating degenerative disc disease in an intervertebral disc having a nucleus pulposus, comprising the steps of:

a) administering a formulation comprising at least two highly specific antagonists of pro-inflammatory cytokines selected from the group consisting of TNF-α, an interleukin (preferably, IL-1, Il-6 and IL-8), FAS, an FAS ligand, and IFN-gamma.

Preferably, at least one of the substances is an antagonist of TNF-α. Preferably, the other substance is an antagonist of an interleukin.

In some embodiments, the formulation comprises a suitable biocompatible carrier such as saline. In some embodiments, the carrier is selected from the carriers disclosed in U.S. Pat. No. 6,277,969 ("Le"), the specification of which is incorporated by reference in its entirety.

Also in accordance with the present invention, there is provided a formulation for treating degenerative disc disease, comprising:

a) a high specificity cytokine antagonist, and
b) a second therapeutic agent selected from the group consisting of:
  i) a growth factor, and
  ii) viable cells.

In some embodiments of this formulation, the high specificity cytokine antagonist is selected from the group consisting of antagonists of TNF and antagonists of an interleukin.

Because the causes of low back pain may be myriad, and because of the significant cost of many of these specialized HSCAs, it would be useful for the clinician to first perform a diagnostic test in order to confirm that the targeted disc in fact possesses high levels of the targeted cytokine prior to providing the injection.

In one embodiment, the diagnostic test comprises a non-invasive diagnostic test comprising using an MRI.

Preferably, the clinician would first perform a discogram in order to identify which disc or discs are responsible for the patient's low back pain. Next, the clinician would perform an invasive or non-invasive test upon the targeted disc in order to confirm the presence of or quantify the level of the pro-inflammatory cytokine.

In one embodiment, the diagnostic test comprises an invasive test in which a portion of the disc is removed and analyzed. In some embodiments, the clinician removes a portion of the nucleus pulposus. In others, the clinician removes a portion of the annulus fibrosus. Preferably, the removed material is a portion of the nucleus pulposus. The presence of pro-inflammatory cytokines in the removed material may detected by procedures including but not limited to electrophoresis, or an enzyme-linked immunoabsorbent assay (as per Burke, *Br. JBJS*, 84-B(2), 2002).

In some embodiments, the diagnostic methods disclosed in U.S. Pat. No. 6,277,969 ("Le"), the specification of which is incorporated by reference in its entirety, are selected. In these methods, high specificity anti-TNF-α compounds are used as diagnostic tools for detecting TNF-alpha in the patient known or suspected to have a high level of TNF-alpha.

After determining the levels of the different pro-inflammatory cytokines in the degenerating disc, the clinician will preferably proceed to compare these diagnosed levels against pre-determined levels of the pro-inflammatory cytokines. If the diagnosed level of the pro-inflammatory cytokine exceeds the pre-determined level, then the clinician may conclude that these higher levels are causing unwanted inflammatory action and proceed to directly inject a specific HSCA into the disc capable of inhibiting the targeted protein.

In some embodiments, the predetermined level for an interleukin is at least 100 pg/ml. In some embodiments, the pre-determined level for IL-6 is at least 250 pg/ml. In some embodiments, the predetermined level for IL-8 is at least 500 pg/ml. In some embodiments, the predetermined level for PGE2 is at least 1000 pg/ml. In some embodiments, the predetermined level for TNF-α is at least 500 pg/ml. In others, the predetermined level for TNF-α is at least 20 pg/ml, more preferably at least 30 pg/ml, more preferably at least 50 pg/ml, more preferably at least 1 ng/ml. In others, the predetermined level for TNF-α is at least 1 ng/disc.

It would also be useful to be able to determine whether directly administering the therapeutic substances of the present invention was in fact efficacious. Accordingly, one can measure the level of cytokine remaining in the disc after administration.

It is further believed that the present invention can also be used to prevent degeneration of an intervertebral disc in a human individual, namely, by following a procedure comprising the steps of:
 a) determining a genetic profile of the individual,
 b) comparing the profile of the individual against a pre-determined genetic profile level of at-risk humans,
 c) determining that the individual is at at-risk patient, and
 d) injecting an antagonist of the pro-inflammatory protein into a disc of the individual.

EXAMPLE I

This non-limiting prophetic example describes how to transdiscally administer a formulation comprising a HSCA and saline into a nucleus pulposus of a degenerating disc.

First, the clinician uses a diagnostic test to verify that a particular disc within a patient has high levels of a particular pro-inflammatory cytokine.

Next, the clinician provides a local anesthetic (such as 5 ml lidocaine) to the region dorsal of the disc of concern to reduce subcutaneous pain.

Next, the clinician punctures the skin of the patient dorsal the disc of concern with a relatively large (e.g., 18-19 gauge) needle having a stylet therein, and advances the needle through subcutaneous fat and dorsal sacrolumbar ligament and muscles to the outer edge of the intervertebral disc.

Next, the stylet is removed from the needle.

Next, the clinician receives a syringe having a smaller gauge needle adapted to fit within the larger gauge needle. This needle is typically a 22 or 24 gauge needle. The barrel of the syringe contains the formulation of the present invention.

The formulation contains infliximab, and has an infliximab concentration of between about 30 mg/ml and about 60 mg/ml.

Next, the physician advances the smaller needle co-axially through the larger needle and past the distal end of the larger needle, thereby puncturing the annulus fibrosus. The smaller needle is then further advanced into the center of the nucleus pulposus. Finally, the clinician depresses the plunger of the syringe, thereby injecting between about 0.1 and 1 ml of the formulation into the nucleus pulposus.

EXAMPLE II

This non-limiting prophetic example is substantially similar to that of Example I, except that the formulation comprises a sustained release device comprising the co-polymer poly-DL-lactide-co-glycolide (PLG). The formulation contains infliximab as the antagonist, and has an infliximab concentration of between about 30 mg/ml and 5 about 60 mg/ml.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting degeneration of an extracellular matrix of a nucleus pulposus of an intervertebral disc having a degenerating nucleus pulposus and an annulus fibrosus in a patient in need thereof, comprising transdiscally administering into the degenerating nucleus pulposus an effective amount of a formulation comprising a highly specific cytokine antagonist that inhibits tumor necrosis factor-α (TNF-α), wherein said highly specific cytokine antagonist is released from a sustained release device comprising a hydrogel, thereby effectively inhibiting the degeneration of the extracellular matrix of the degenerating nucleus pulposus of the intervertebral disc.

2. The method of claim 1, wherein said highly specific cytokine antagonist is a monoclonal antibody.

3. A method of inhibiting degeneration of an extracellular matrix of a nucleus pulposus of an intervertebral disc having a degenerating nucleus pulposus in a patient in need thereof, comprising transdiscally administering into the degenerating nucleus pulposus an effective amount of a formulation comprising infliximab, wherein said infliximab is released from a a sustained release device comprising a hydrogel, thereby effectively inhibiting the degeneration of the extracellular matrix of the degenerating nucleus pulposus of the intervertebral disc.

4. The method of claim 2, wherein said monoclonal antibody binds membrane-bound TNF-α.

5. The method of claim 2, wherein said monoclonal antibody binds soluble TNF-α.

6. The method of claim 1, wherein said highly specific cytokine antagonist is released from said formulation by its diffusion through said sustained delivery device.

7. The method of claim 1, wherein said highly specific cytokine antagonist is released from said formulation by biodegradation of said sustained delivery device.

8. The method of claim 1, wherein the sustained release device provides controlled release.

9. The method of claim 1, wherein the sustained release device provides continuous release.

10. The method of claim 1, wherein the sustained release device provides intermittent release.

11. The method of claim 1, wherein the sustained release device comprises a biosensor.

12. The method of claim 1, wherein the sustained release device comprises a plurality of microspheres.

13. The method of claim 1, wherein said sustained release device is adapted to remain in said intervertebral disc for at least 1 month.

14. The method of claim 13, wherein said sustained release device is adapted to remain in said intervertebral disc for at least 2 months.

15. The method of claim 14, wherein said sustained release device is adapted to remain in said intervertebral disc for at least 6 months.

16. The method of claim 1, wherein the formulation is provided closely adjacent to the outer wall of the annulus fibrosus.

17. The method of claim 1, further comprising removing a portion of the nucleus pulposus prior to administering an effective amount of said formulation.

18. The method of claim 1, wherein said formulation is administered in a volume of between 0.03 ml and 1.0 ml.

19. A method of treating degenerative disc disease in an intervertebral disc having a nucleus pulposus and an annulus fibrosus in a patient in need thereof, comprising transdiscally administering into an intervertebral disc an effective amount of a formulation comprising a highly specific cytokine antagonist that inhibits tumor necrosis factor-α (TNF-α), wherein said highly specific cytokine antagonist is (a) administered in an amount effective to inhibit degradation of an extracellular matrix of the nucleus pulposus and (b) released from a sustained release device, wherein said sustained release device comprises a hydrogel, thereby effectively treating the degenerative disc disease in the intervertebral disc.

* * * * *